US00PP16467P2

(12) United States Plant Patent
Bradford

(10) Patent No.: US PP16,467 P2
(45) Date of Patent: Apr. 18, 2006

(54) NECTARINE TREE NAMED 'WESTERN BRIGHT'

(50) Latin Name: *Prunus persica*
Varietal Denomination: Western Bright

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 107 days.

(21) Appl. No.: 11/029,690

(22) Filed: Jan. 6, 2005

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP5,228 P * 5/1984 Zaiger ..... Plt./190
PP7,507 P * 4/1991 Bradford et al. ..... Plt./190
PP8,948 P 10/1994 Bradford
PP10,250 P * 2/1998 Zaiger et al. ..... Plt./190
PP11,968 P2 * 7/2001 Bradford ..... Plt./190

* cited by examiner

*Primary Examiner*—Anne Marie Grunberg
*Assistant Examiner*—W. C. Haas

(57) ABSTRACT

The present invention relates to a nectarine tree, *Prunus persica,* and more particularly to a new and distinct variety broadly characterized by a medium size, vigorous, hardy, self-fertile, productive and regular bearing tree. The fruit matures under the ecological conditions described in mid June, with the first picking on Jun. 11, 2004. The fruit is uniformly large in size, mildly acidic and sweet in flavor, globose in shape, clingstone in type, firm in texture, yellow in flesh color, and virtually full red in skin color. The variety was developed as a first generation cross using 'Diamond Ray' (U.S. Plant Pat. No. 8,948) yellow flesh nectarine as the selected seed parent and an unnamed yellow flesh clingstone nectarine as the selected pollen parent.

1 Drawing Sheet

Latin name: *Prunus persica.*
Varietal denomination: 'Western Bright'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'Western Bright'. The present variety was hybridized by me in 1996, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'Diamond Ray' (U.S. Plant Pat. No. 8,948) yellow flesh nectarine as the selected seed parent and an unnamed yellow flesh clingstone nectarine (unpatented) as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to its selected seed parent, 'Diamond Ray' (U.S. Plant Pat. No. 8,948) nectarine, by producing nectarines that are large in size, nearly globose in shape, very firm in texture, clingstone in type, yellow in flesh color, and nearly full red in skin color, but is distinguished therefrom by having globose instead of reniform leaf glands, by having a bitter instead of sweet kernel, and by producing fruit that has less skin freckling and that ripens about 12 days earlier.

SUMMARY OF VARIETY

In summary, the present variety is characterized by a medium size, vigorous, hardy, self-fertile, productive and regular bearing tree. The fruit matures under the ecological conditions described in the mid June, with the first picking on Jun. 11, 2004. The fruit is uniformly large in size, mildly acidic and sweet in flavor, globose in shape, clingstone in type, firm in texture, yellow in flesh color, and virtually full red in skin color. The variety was developed as a first generation cross using 'Diamond Ray' (U.S. Plant Pat. No. 8,948) yellow flesh nectarine as the selected seed parent and an unnamed yellow flesh clingstone nectarine as the selected pollen parent.

DRAWING

The accompanying photograph exhibits four whole fruits positioned to display the characteristics of the skin color and form, one fruit divided transversely to the suture plane to reveal the flesh and stone, and typical leaves.

DETAILED BOTANICAL DESCRIPTION

Referring now more specifically to the pomological characteristics of this new and distinct variety of nectarine tree, the following has been observed under the ecological conditions prevailing near Le Grand, Merced County (San Joaquin Valley), Calif. and was developed at the state of full ripeness on Jun. 20, 2004, on the original tree during its eighth growing season. It is to be noted that the 2004 stone fruit season was abnormally early in maturing times for all varieties, thus skewing the starting calendar dates approximately two weeks forward. All major color code designations are by reference to the Inter-Society Color Council, National Bureau of Standards. Common color names are also used occasionally.

TREE

Size: Medium, reaching and maintaining a height of 12' [3.7 m.] and a spread of 10' [3.1 m.] after eight growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to be vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Very productive, thinning usually necessary.

Fertility: Self-fertile.

Bearing: Regular bearer with no alternate bearing observed.

Trunk:

*Size.*—Medium, reaching a diameter of 4⅞" [124 mm.] measured 12" above the ground after the eighth growing season.

*Texture.*—Shaggy.

*Bark color.*—A Grayish brown [61. gy.Br] and Dark yellowish brown [78. d.yBr] variegation.

*Lenticels.*—Approximate Number Per Square Inch: 8. Color: Light yellowish brown [76. l.yBr]. Average Size: ⅜" [9.5 mm.]. Shape: Eye-shaped to elongated.

Branches:

*Size.*—Diameter of the main scaffold is 3" [76 mm.] measured 12" above the crotch, diameter of typical limb is 2¼" [57 mm.] measured 12" above the first fork, typical of *Prunus persica,* and dependent upon cultural practices and climatic conditions.

*Texture.*—Smooth on first year wood, increasing roughness with age.

*Color.*—1st Year Wood Topside: Grayish red [19. gy.R]. 1st Year Wood Underside: Brilliant yellow green [116. brill.YG]. Older Wood: Deep yellowish brown [75. deep yBr].

*Lenticels.*—Number Per Square Inch: More than 40 on second year wood. Color: Moderate orange yellow [71. m.OY]. Typical size: 1/16" [1.6 mm.] to 3/16" [4.8 mm.]. Shape: Eye-shaped to elongated.

Leaves:

*Size.*—Medium. Average Length: 5⅞" [149 mm.]. Average width: 1⅝" [41 mm.].

*Arrangement.*—Alternate.

*Thickness.*—Medium.

*Form.*—Elliptical.

*Apex.*—Acutely pointed.

*Base.*—Acute with an average base angle of 75 degrees.

*Surface.*—Smooth.

*Color.*—Dorsal Surface: Dark olive green [126. d.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: ⅜" [9.5 mm.]. Average Thickness: 1/16" [1.6 mm.]. Color: Light yellow green [119. l.YG].

*Stipules.*—Number: 2 per leaf, up to 6 per growing tip. Average Length: ¼" [6.4 mm.]. Color: Very yellow green [115. v.YG] becoming Dark yellowish brown [78. d.yBr] with maturity.

*Glands.*—Number: 2 to 3 per leaf. Position: Alternate, positioned on petiole and base of leaf blade. Size: Small. Form: Globose. Color: Pale yellow green [121. p.YG] when young and Grayish reddish brown [46. gy.rBr] with age.

*Leaf buds.*—Medium, pointed.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Strong purplish pink [247. s.pPk].

Flowers: Perfect, complete, perigynous, usually a single pistil, typically thirty or more stamens, five sepals and petal locations alternately positioned.

*Type.*—Showy, large.

*Average flower diameter.*—1 13/16" [46.0 mm.].

*Number of petals.*—Usually five, with a small percentage of double blossoms observed.

*Petal shape.*—Circular.

*Petal margin.*—Somewhat wavy.

*Average petal diameter.*—¾" [19.1 mm.].

*Average petal length.*—13/16" [20.6 mm.].

*Petal apex.*—Rounded.

*Petal base.*—Rounded to slightly truncate.

*Petal color.*—Pale pink [7. p.Pk] toward the apex and Dark purplish pink [251. d.pPk] toward the base.

*Anther color.*—Deep red [13. deep R] over a Light orange yellow [70. l.OY] center.

*Stigma color.*—Light greenish yellow [101. l.gY].

*Sepal color.*—Very deep purplish red [257. v.deep pR].

*Sepal length.*—9/32" [7.2 mm.].

*Sepal width.*—¼" [6.4 mm.].

*Average pistil length.*—⅝" [15.9 mm.].

*Average stamen length.*—9/16" [14.3 mm.].

*Fragrance.*—Moderate.

*Blooming period.*—Early to medium compared with other varieties.

*Onset of bloom.*—One percent on Feb. 25, 2004.

*Date of full bloom.*—Mar. 6, 2004.

*Duration of bloom.*—One to two weeks, dependent on ambient temperature.

*Number per cluster.*—1 to 3 with single flowers most common.

FRUIT

Maturity when described: Full ripe, Jun. 22, 2004.

Date of first picking: Jun. 13, 2004.

Date of last picking: Jun. 24, 2004.

Size: Uniform, large.
*Average diameter axially.*—2⅞" [73.0 mm.].
*Average diameter across suture plane.*—2⅞" [73.0 mm.].
*Typical weight.*—8.0 ounces [227 grams].
Form: Uniform, usually symmetrical, globose.
*Longitudinal section form.*—Circular to somewhat oval.
*Transverse section through diameter.*—Circular.
Suture: A moderate groove from the stem to somewhat beyond the pistil point that is sharper and deeper toward both the stem cavity and apex with a marked depression beyond the pistil point.
Ventral surface: Rounded, lipped throughout on both sides, stronger toward the apex.
Lips: Mostly equal with a few unequal.
Cavity: Flaring, stem markings usually present.
*Depth.*—½" [12.7 mm.].
*Breadth.*—1" [25.4 mm.].
Base: Rounded to truncate.
Apex: Rounded.
Pistil point: Both apical and oblique, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Astringent.
*Tendency to crack.*—None observed.
*Color.*—Very dark red [17. v.d.R] smoothly blending into a Strong red [12. s.R] background with a minor amount of Light orange yellow [70. l.OY] freckling toward apex.
Flesh:
*Color.*—Brilliant yellow [83. brill.Y] with sporadic Moderate red [15. m.R] streaking throughout.
*Surface of pit cavity.*—Light yellow [86. l.Y] and Dark red [16. d.R] fibers breaking when twisted from the stone.
*Amygdalin.*—Abundant.
*Juice.*—Abundant, rich.
*Texture.*—Firm, crisp and melting.
*Fibers.*—Abundant, fine.
*Ripens.*—Slightly earlier at apex.
*Flavor.*—Acidic but quite sweet, 14 brix.
*Aroma.*—Moderate.
*Eating quality.*—Very good.

STONE

Type: Clingstone.
Form: Oval.
Hilum: Narrow.
Base: Slightly oblique.
Apex: Acute, with a rounded protrusion about ⅛" [3.2 mm.] in length located at the tip.
Sides: Slightly unequal.
Surface: Irregularly furrowed near apex and pitted toward the base.
Ridges: Jagged toward the base.
External color of stone: Moderate yellowish brown [77. m.yBr].
Pit wall color when cracked: Moderate yellowish brown [77. m.yBr].
Cavity surface color: Strong yellowish brown [74. s.yBr].
Average pit wall thickness: ¼" [6.4 mm.].
Average width: 1⅛" [28.6 mm.].
Average length: 1 9/16" [39.7 mm.].
Average breadth: ⅞" [22.2 mm.].
Tendency to split: Rarely observed.
Kernel:
*Form.*—Oval.
*Skin color.*—Light yellow [86. l.Y].
*Pellicle color.*—Moderate yellowish brown [77. m.yBr].
*Vein color.*—Strong yellowish brown [74. s.yBr].
*Taste.*—Bitter.
*Viable.*—Yes.
*Average width.*—9/16" [14.3 mm.].
*Average length.*—13/16" [20.6 mm.].
*Amygdalin.*—Abundant.

USE

Market: Fresh market and long distance shipping.
Keeping quality: Good. Fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its selected seed parent, 'Diamond Ray' (U.S. Plant Pat. No. 8,948) nectarine, by producing nectarines that are large in size, nearly globose in shape, very firm in texture, clingstone in type, yellow in flesh color, and nearly full red in skin color, but is distinguished therefrom by having globose instead of reniform leaf glands, by having a bitter instead of sweet kernel, and by producing fruit that has less skin freckling and that ripens about 12 days earlier.

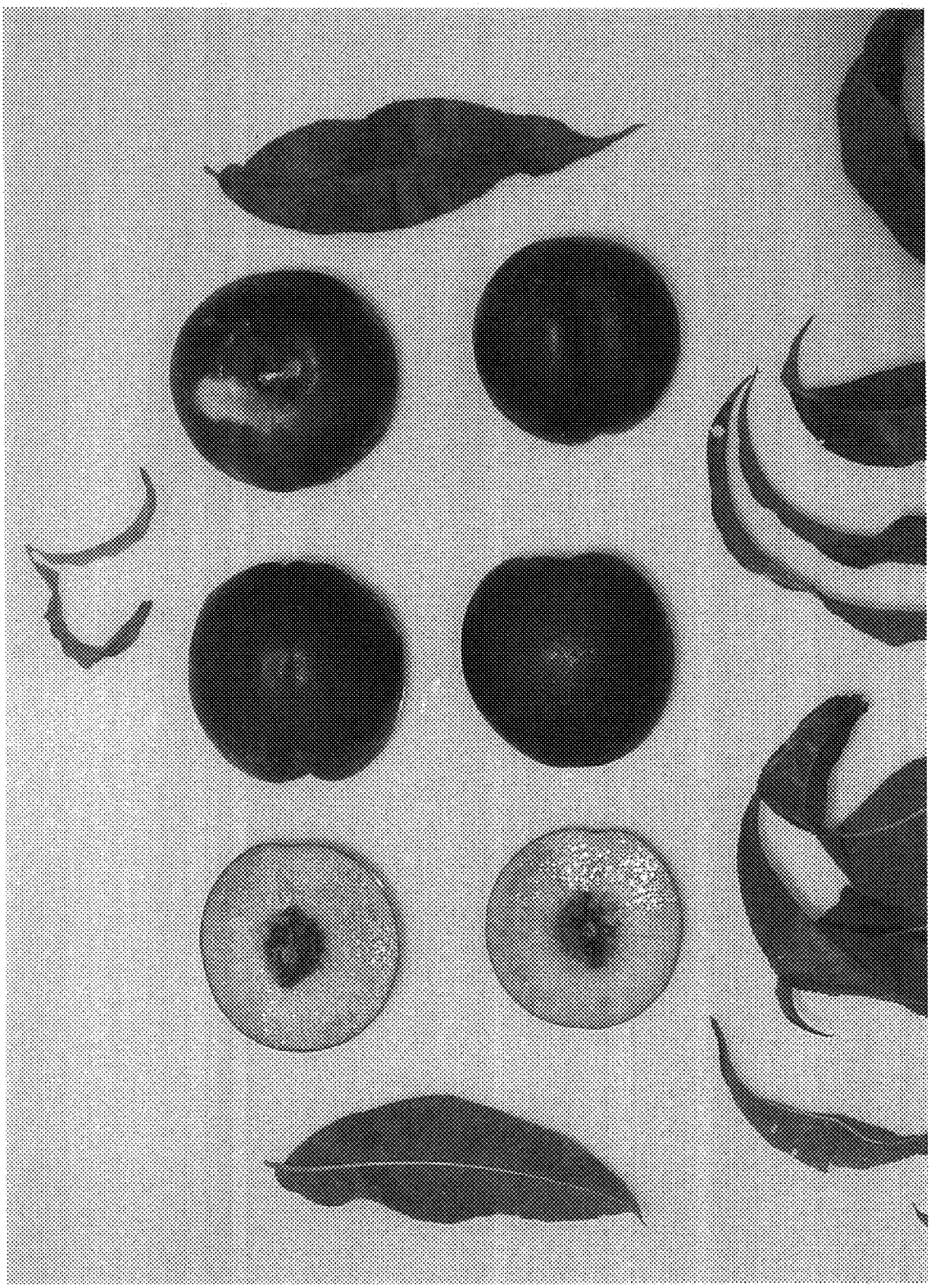

* * * * *